(12) United States Patent
Kokones et al.

(10) Patent No.: US 6,970,747 B2
(45) Date of Patent: Nov. 29, 2005

(54) NEUROSTIMULATION LEAD STYLET HANDLE

(76) Inventors: Scott B. Kokones, 410 Second St. #148, Minneapolis, MN (US) 55401; Shahn S. Sage, 832-140th Lane NW., Andover, MN (US) 55304

( * ) Notice: Subject to any disclaimer, the term of this patent is extended or adjusted under 35 U.S.C. 154(b) by 107 days.

(21) Appl. No.: 10/045,553

(22) Filed: Jan. 11, 2002

(65) Prior Publication Data

US 2003/0135253 A1    Jul. 17, 2003

(51) Int. Cl.⁷ .............................. A61N 1/05
(52) U.S. Cl. ............... 607/116; 604/177; 604/178; 600/585
(58) Field of Search ............ 607/115–117; 604/164.13, 604/165.03, 528, 177, 164.04, 164.11, 526; 600/434, 585

(56) References Cited

U.S. PATENT DOCUMENTS

| | | | |
|---|---|---|---|
| 4,257,427 A * | 3/1981 | Bucalo ..................... 600/582 |
| 4,683,896 A * | 8/1987 | Herbst et al. ............... 607/116 |
| 4,850,359 A * | 7/1989 | Putz ......................... 600/377 |
| 4,960,134 A * | 10/1990 | Webster, Jr. ................ 607/116 |
| 5,047,018 A | 9/1991 | Gay et al. |
| 5,163,912 A | 11/1992 | Gay et al. |
| 5,228,455 A * | 7/1993 | Barcel ....................... 607/127 |
| 5,324,260 A | 6/1994 | O'Neill et al. |
| 5,360,406 A | 11/1994 | Boykin et al. |
| 5,376,109 A | 12/1994 | Lindegren et al. |
| 5,395,331 A | 3/1995 | O'Neill et al. |
| D359,801 S | 6/1995 | Boykin et al. |
| 5,448,993 A * | 9/1995 | Lynch et al. ................. 600/434 |
| 5,620,418 A | 4/1997 | O'Neill et al. |
| 5,749,371 A * | 5/1998 | Zadini et al. ............... 600/585 |
| 5,807,326 A | 9/1998 | O'Neill et al. |
| 5,948,008 A * | 9/1999 | Daikuzono .................... 607/89 |
| 6,178,354 B1 * | 1/2001 | Gibson ....................... 607/116 |
| 6,233,488 B1 * | 5/2001 | Hess .......................... 607/58 |
| 6,371,940 B1 * | 4/2002 | Valencia et al. ......... 604/164.13 |
| 6,510,347 B2 * | 1/2003 | Borkan ....................... 607/117 |

FOREIGN PATENT DOCUMENTS

| | | |
|---|---|---|
| EP | 0450181 A1 | 10/1991 |
| WO | WO 01/21243 A1 | 3/2001 |

* cited by examiner

Primary Examiner—Jeffrey R. Jastrzab
(74) Attorney, Agent, or Firm—John W. Albrecht; Eric R. Waldkoetter (57) ABSTRACT

An implantable neurological stimulation lead with improved stylet handle comprises a lead body, at least one conductor, at least one electrical contact, at least one electrode, a stylet wire, and a stylet handle. The lead body has a body proximal end, a body distal end, and a stylet lumen. The conductor is contained in the lead and extends from the body proximal end to the body distal end, and the conductor is electrically insulated. The electrical connector is carried on the body proximal end and electrically connected to the conductor. The electrode is carried on the body distal end and electrically connected to the conductor. The stylet wire is configured for insertion into the stylet lumen to stiffen the lead body. The stylet handle is selectively coupled to the stylet wire. The stylet handle has a lead carrier and at least one gripper carried in the lead carrier configured to grip the lead body at a selected point along the lead body or lead proximal end.

13 Claims, 9 Drawing Sheets

NEUROSTIMULATION LEAD STYLET HANDLE

FIELD OF THE INVENTION

This disclosure relates to a medical device and more particularly to implantable neurological electrical stimulators and implantable electrical stimulation leads.

BACKGROUND OF THE INVENTION

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life. One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension such as shown in Medtronic, Inc. brochure "Implantable Neurostimulation System" (1998). More specifically, the neurostimulator system can be an Itrel II® Model 7424 or an Itrel 3® Model 7425 available from Medtronic, Inc. in Minneapolis, Minn. that can be used to treat conditions such as pain, movement disorders and pelvic floor disorders. The neurostimulator is typically connected to a stimulation lead that has one or more electrodes to deliver electrical stimulation to a specific location in the patient's body.

The lead and stylet combination are part of the implantable neurostimulation system. The neuro stimulation lead is placed in the desired location of the body. The stylet wire and handle combination are used to give the lead stiffness during implantation and to aid in maneuvering the lead into the desired position. Currently several types of lead and stylet combinations exist for this purpose. An example of a stylet that engages the proximal end of the lead connector region in specified locations is the Pisces Quad Lead Model 3487A stylet available from Medtronic, Inc., Minneapolis, Minn., USA. The location of the distal end of the stylet can potentially reside in different locations in the electrode region due to tolerances in both the lead and the stylet. Another combination offers a stylet that terminates at a definite point in the distal end of the lead and a handle that engages the lead at specific points at the lead proximal end. For this stylet lead combination each stylet must be custom made to fit each lead. All custom fit stylets are packaged in the lead kit. If a physician requires the use of a different stylet, a stylet from another kit may not work as intended. A third type of lead stylet system exits where the stylet terminates at a specific point in the distal end of the lead, but does not engage the lead at the proximal end. This makes maneuvering the lead more difficult. An example of a stylet handle is shown in U.S. Pat. No. 6,203,506 "Operating Device For A Stylet Unit" by Boström (Mar. 20, 2001).

Thus, embodiments of the implantable neurological stimulation lead with improved stylet handle are disclosed that improve physician stimulation lead placement control and reduce manufacturing cost.

BRIEF SUMMARY OF THE INVENTION

An implantable neurological stimulation lead with improved stylet handle comprises a lead body, at least one conductor, at least one electrical contact, at least one electrode, a stylet wire, and a stylet handle. The lead body has a body proximal end, a body distal end, and a stylet lumen. The conductor is contained in the lead and extends from the body proximal end to the body distal end, and the conductor is electrically insulated. The electrical connector is carried on the body proximal end and electrically connected to the conductor. The electrode is carried on the body distal end and electrically connected to the conductor. The stylet wire is configured for insertion into the stylet lumen to stiffen the lead body. The stylet handle is selectively coupled to the stylet wire. The stylet handle has a lead carrier and at least one gripper carried in the lead carrier configured to grip the lead body at a selected point along the lead body or lead proximal end. Many embodiments and methods of operation of the implantable neurological stimulation lead with improved stylet handle are possible.

DETAILED DESCRIPTION OF THE INVENTION

Figure 1:
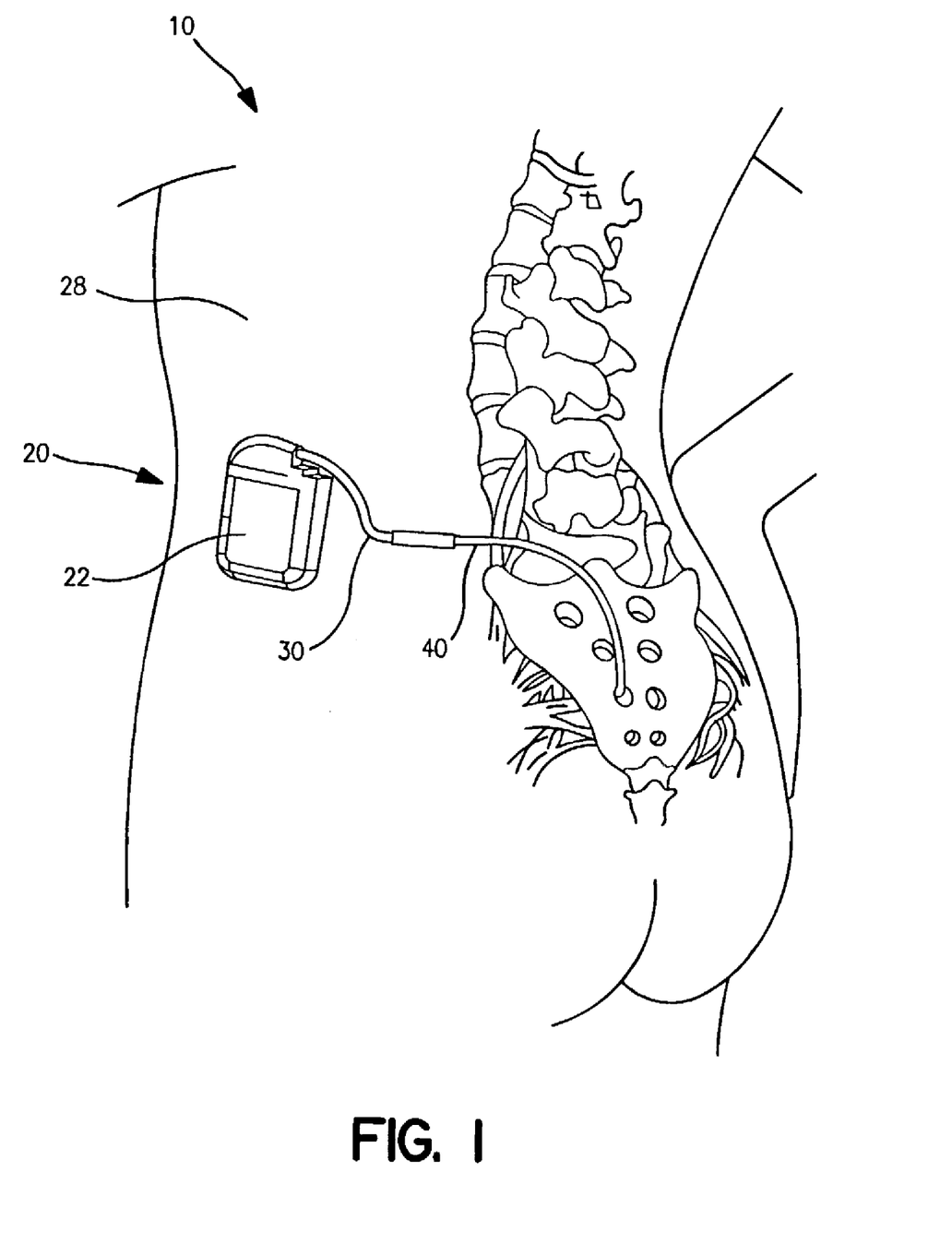
FIG. 1 shows a general environmental view for a neurostimulation system embodiment.

FIG. 1 shows a general environmental view 10 for an implantable neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II® Model 7424 or an Itrel 3® Model 7425 available from Medtronic, Inc. in Minneapolis, Minn., a stimulation lead extension 30, and a stimulation lead 40. The neurostimulator 22 is typically implanted subcutaneously in the patient's body 28 at a location selected by the clinician. The stimulation lead 40 is typically fixed in place near the location selected by the clinician using a device such as an adjustable anchor.

Figure 2:
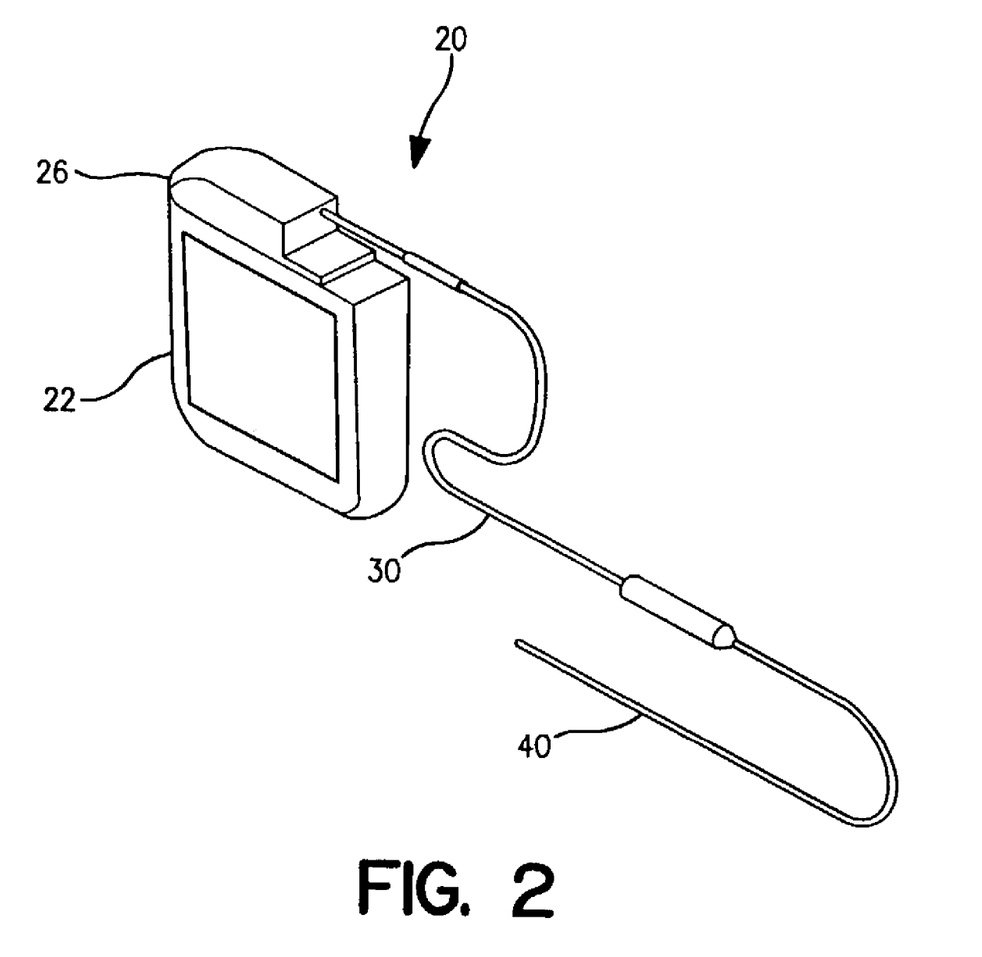
FIG. 2 shows a neurostimulation system embodiment.

FIG. 2 shows an implantable neurostimulation system 20 comprising an implantable neurostimulator 22, a stimulation lead 40, and a lead extension 30. The implantable neurostimulator 22 has a housing, a power supply carried in the housing, and stimulation electronics coupled to the battery and coupled to a connector block 26, which is also known as a terminal block. The implantable neurological stimulator 22 can be a Medtronic Itrel II® Model 7424 or an Itrel 3® Model 7425 or the like, both of which are commercially available. The neurological monitor can be a Medtronic Neurodiagnostics Keypoint monitoring system.

Figure 3:
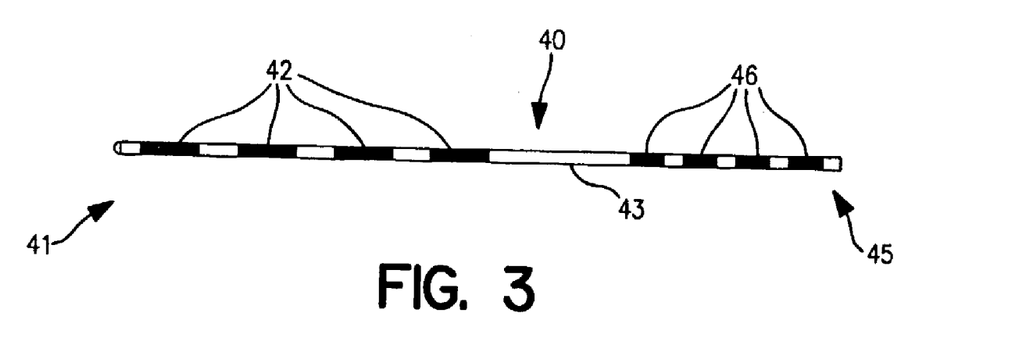
FIG. 3 shows a neurostimulation lead embodiment.
Figure 4:
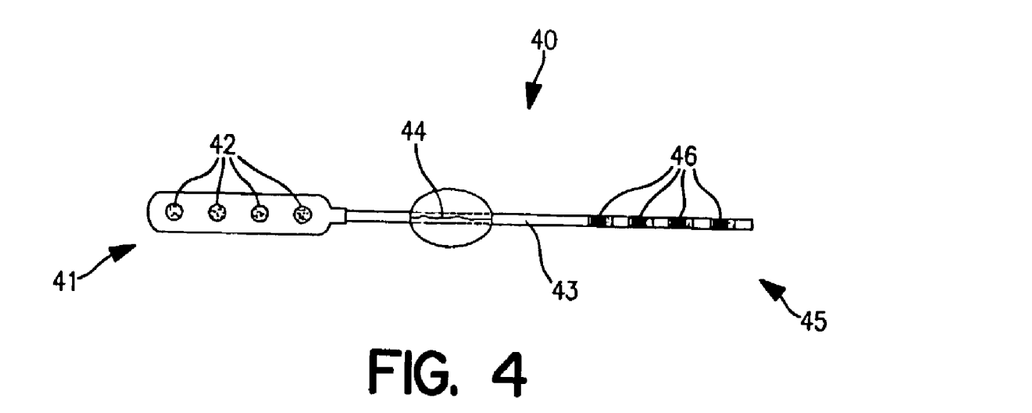
FIG. 4 shows another neurostimulation lead embodiment.
Figure 5:
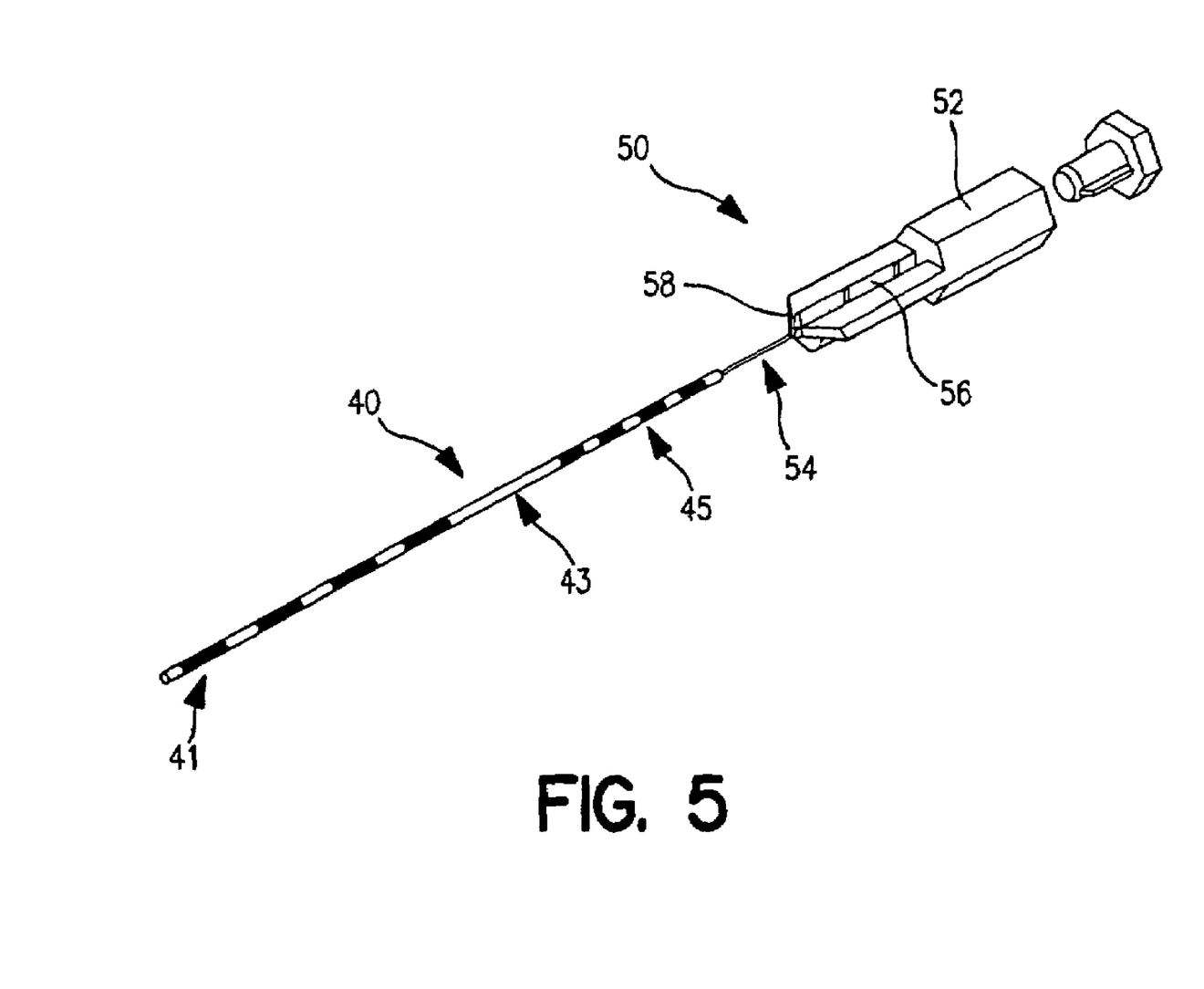
FIG. 5 shows a stimulation lead and stylet handle embodiment.
Figure 6:
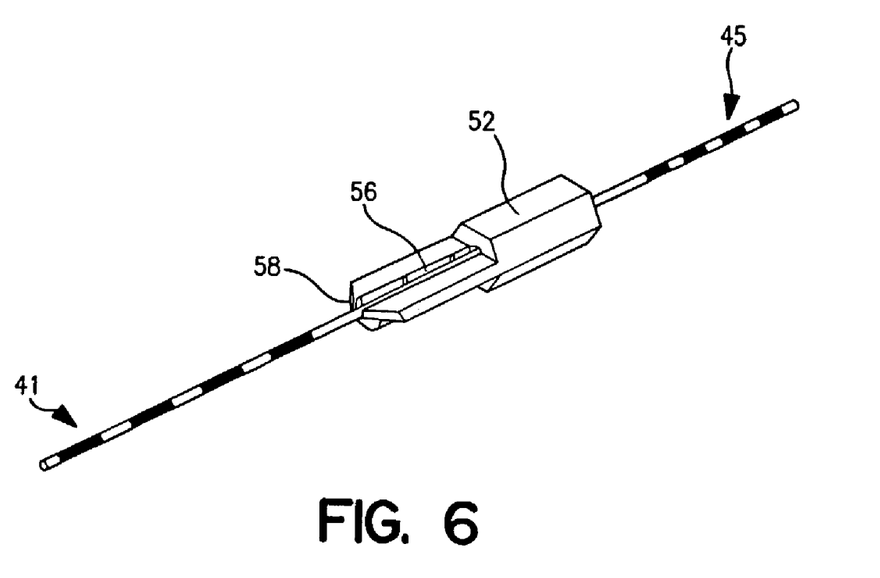
FIG. 6 shows a stimulation lead and another stylet handle embodiment.
Figure 7:
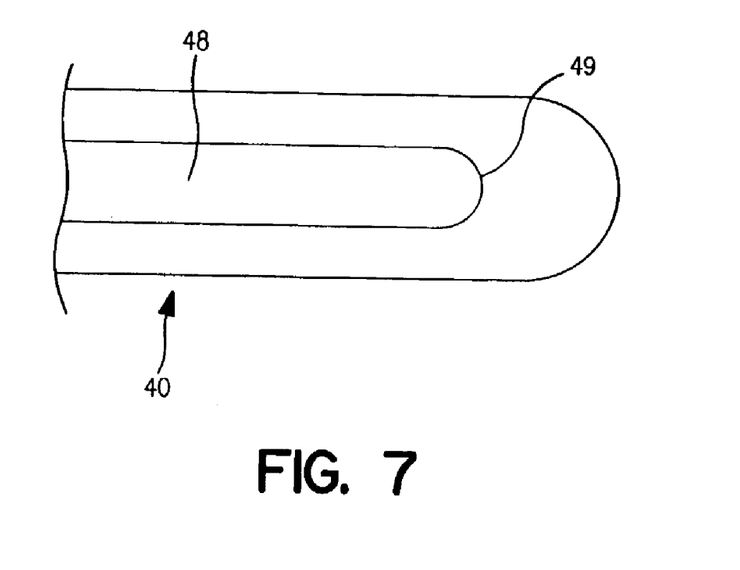
FIG. 7 shows a cross section of stimulation lead distal end with a stylet stop embodiment.
Figure 8:
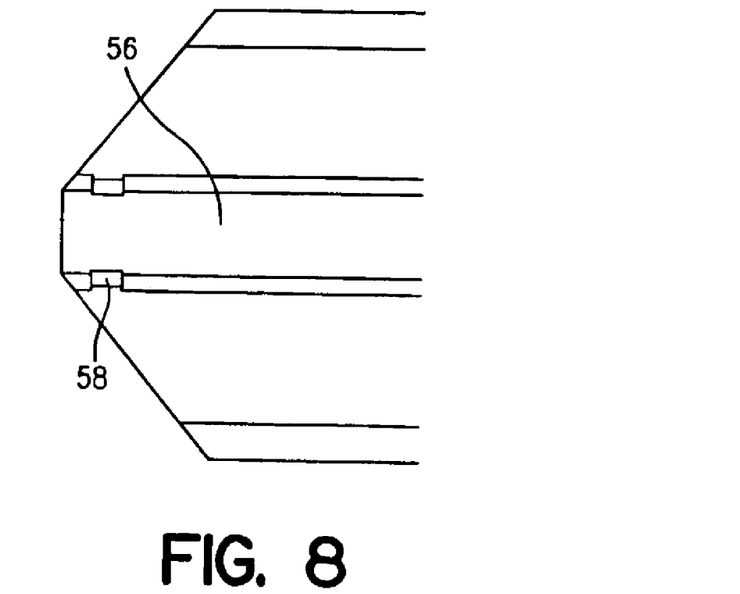
FIG. 8 shows an enlarged drawing of a gripper embodiment.

FIG. 3 shows a percutaneous neurological stimulation lead, and FIG. 4 shows a surgical paddle stimulation lead. The neurological lead 40 can be configured as a neurological stimulation lead, a neurological sensing lead, and a combination of both as a neurological stimulation and sensing lead. The implantable neurological stimulation lead 40 with improved stylet handle 52 comprises a lead body 43, at least one conductor 44, at least one electrical connector 46, at least on electrode 42, and a stylet 50. The lead body 43 has a body proximal end 45, a body distal end 41, and a stylet lumen 48. The lead body 43 can be composed of a wide variety of materials and configurations. Materials can include, but not be limited to silicone rubber, polyurethane, fluoropolymers and the like. Configurations could include monolumen and multilumen tubings. The lead body 43 can be configured with a stylet stop 49 in the lead distal end 41. The stylet stop 49 provides a place for the stylet wire 54 to contact before the lead body 43 is griped. The stylet stop 49 controls where the stylet wire 54 terminates in the stimulation lead 40. With the use of a stylet stop 49 every stimulation lead 40 will have the stylet wire 54 terminate at the same position. This increases the consistency of maneuvering the stimulation lead 40 in the body 28 by a clinician.

The conductor 44, electrical connector 46 and electrode 42 provide an electrical path through the lead body 43. The conductor 44 is contained in the lead 40 extending from the body proximal end 45 to the body distal end 41. The conductor 44 can be manufactured from materials such as MP35N, silver drawn filled tubing (Ag-DFT), Platinum iridium alloys, platinum and the like. Conductor 44 configurations could include stranded, braided or solid wire configured in linear or helical coil arrangements. The conductor 44 is electrically insulated with a polymer. The polymer could be, but is not limited to, ethylene tetrafluoroethylene (ETFE), polytetrafluoroethylene (PTFE), silicone rubber or polyurethane. Other materials that act as electrical insulators can be used. The electrical connector 46 is carried on the body proximal end 45 and electrically connected to the conductor 44. The electrical connector 46 is configured to couple to the implantable neurological stimulator 22 or neurological monitor. The electrode 42 is carried on the body distal end 41 and electrically connected to the conductor 44.

FIGS. 5–11 show various views and embodiments of the implantable neurological stimulation lead 40 with improved stylet handle 52. The stylet 50 includes a stylet wire 54 and a stylet handle 52 which may be selectively coupled. The stylet wire 54 is configured for insertion into the stylet lumen 48 to stiffen the lead body 43. Materials can include, but not be limited to stainless steel and tungsten. The stylet wire 54 can vary in length and characteristics including but not limited to straight, bent or curved tipped, as well as having a full radius tip or a ball tip. The stylet handle 52 may or may not be connected to the stylet wire 54. The stylet handle 52 has a lead carrier 56 and at least one gripper 58 carried in the lead carrier 56 configured to grip the lead body 43 at a selected but not specific point along the lead body 43 or lead proximal end 45. The selected point can be any point along the lead body 43 other than the lead body distal end 41. The stylet handle 52 can also serve as a means for grasping the lead body 43 selectively coupled to the stylet wire 54, the means for grasping configured to grip the lead body 43 at a selected point along the lead body 43 or lead proximal end 45. The lead carrier 56 is designed so a thumb or forefinger has room to push the stimulation lead 40 into the lead carrier 56. When the lead body 43 is engaged in the lead carrier 56 of the stylet handle 52 the stylet wire 54 remains in contact with the stylet stop 49 in the stylet lumen 48 in the lead body distal end 41. The lead carrier 56 is designed to compensate for the tolerances in both the stimulation lead 40 and the stylet 50. When the stylet wire 54 is engaged in the stylet handle 52 at least one gripper 58 in the stylet carrier 56 must grip the stimulation lead 40. The stylet 50 does not have to be custom made in order to fit a specific stimulation lead 40. Any manufactured stimulation lead 40 will mate with any manufactured stylet 50. Materials for the stylet handle 52 can include, but not be limited to polycarbonate, polypropylene, and polyethermide.

Figure 9:
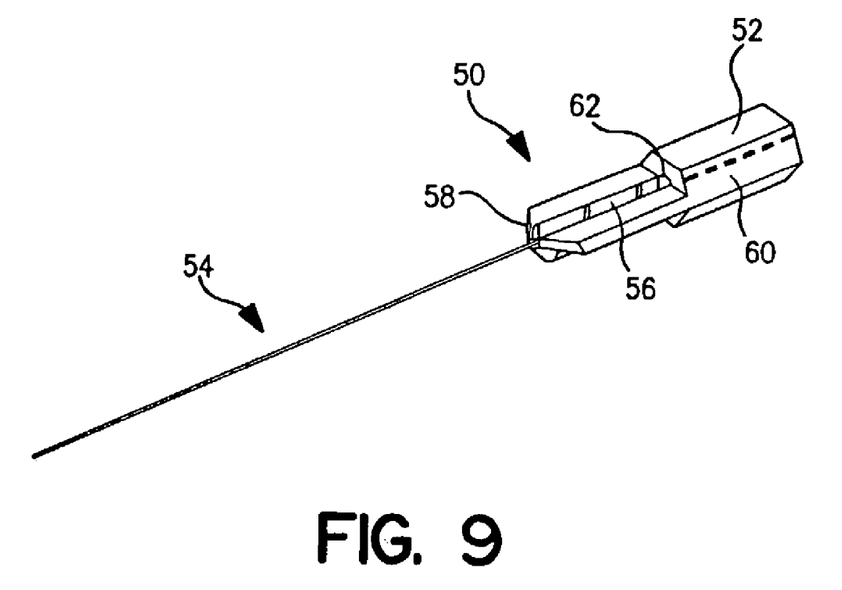
FIG. 9 shows a stylet wire being retained in a stylet handle embodiment.
Figure 10:
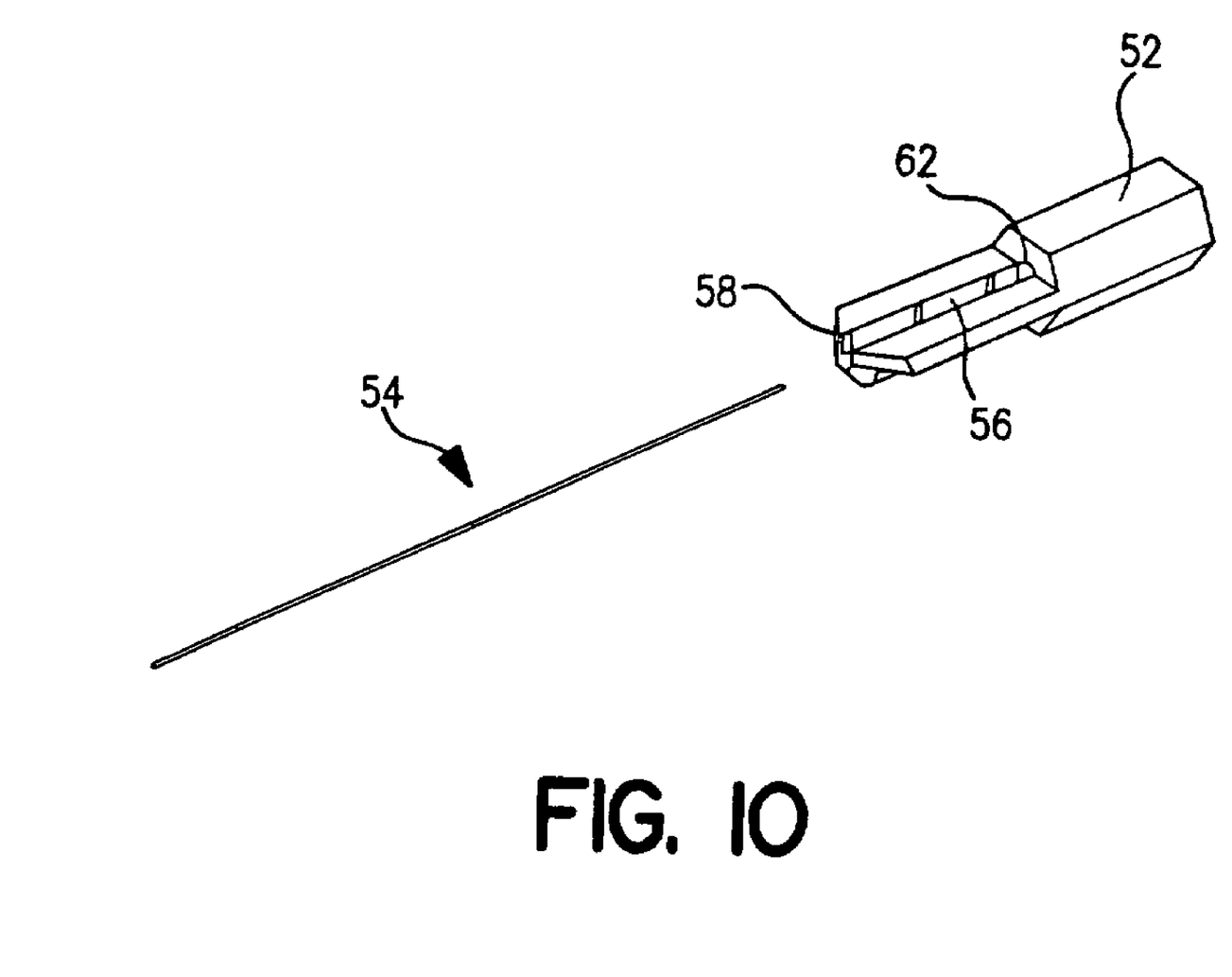
FIG. 10 shows a stylet wire decoupled from a stylet handle embodiment.
Figure 11:
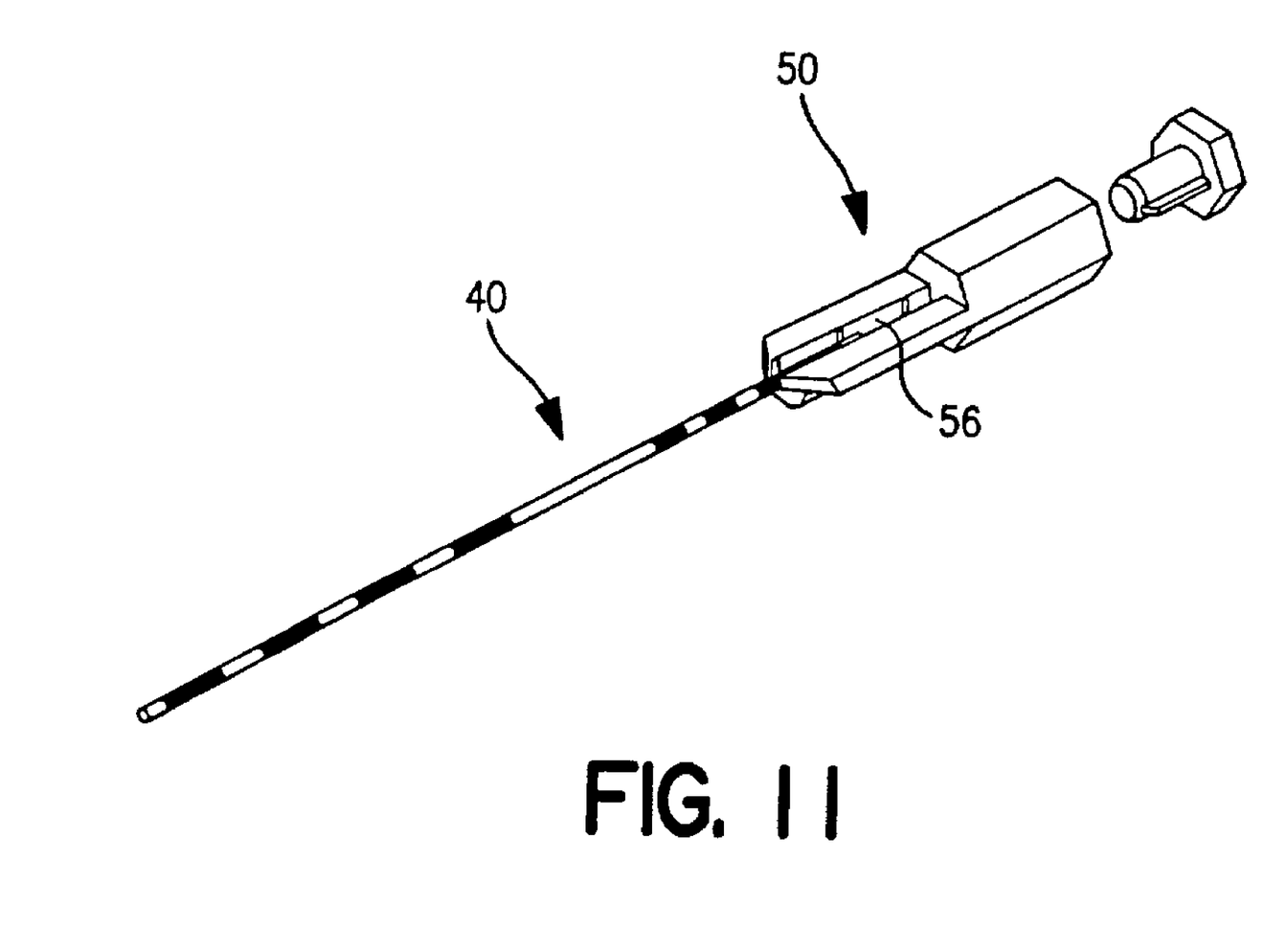
FIG. 11 shows a stimulation lead being gripped by a stylet handle embodiment; and, FIG. 12 shows a flow diagram of a method for inserting a stylet in a stimulation lead embodiment.

Some embodiments of the stylet 50 can include a stylet release 60 in the stylet handle 52. The stylet release 60 has an engaged position where the stylet wire 54 is coupled to the stylet handle 52 and a disengaged position where the stylet wire 54 is decoupled from the stylet handle 52. When the stylet release 60 is disengaged a lead opening 62 is created to permit the stylet handle 52 to be moved toward the lead distal end 41 without being encumbered by the stylet wire 54. The lead proximal end 45 moves completely through the lead opening 62 in the stylet handle 52. This allows the stylet handle 52 to engage the stimulation lead 40 anywhere on the lead body 43 or lead proximal end 45. Engaging the stimulation lead 40 in the lead body 43 allows a physician to torque and maneuver the stimulation lead 40. The stylet handle 52 can be moved from a more proximal position to a distal position on the lead 40 thus increasing the reactivity of the lead distal end 41. As the stimulation lead 40 is pushed into the body 28 the stylet handle 52 can be relocated proximally on the lead body 43.

Figure 12:
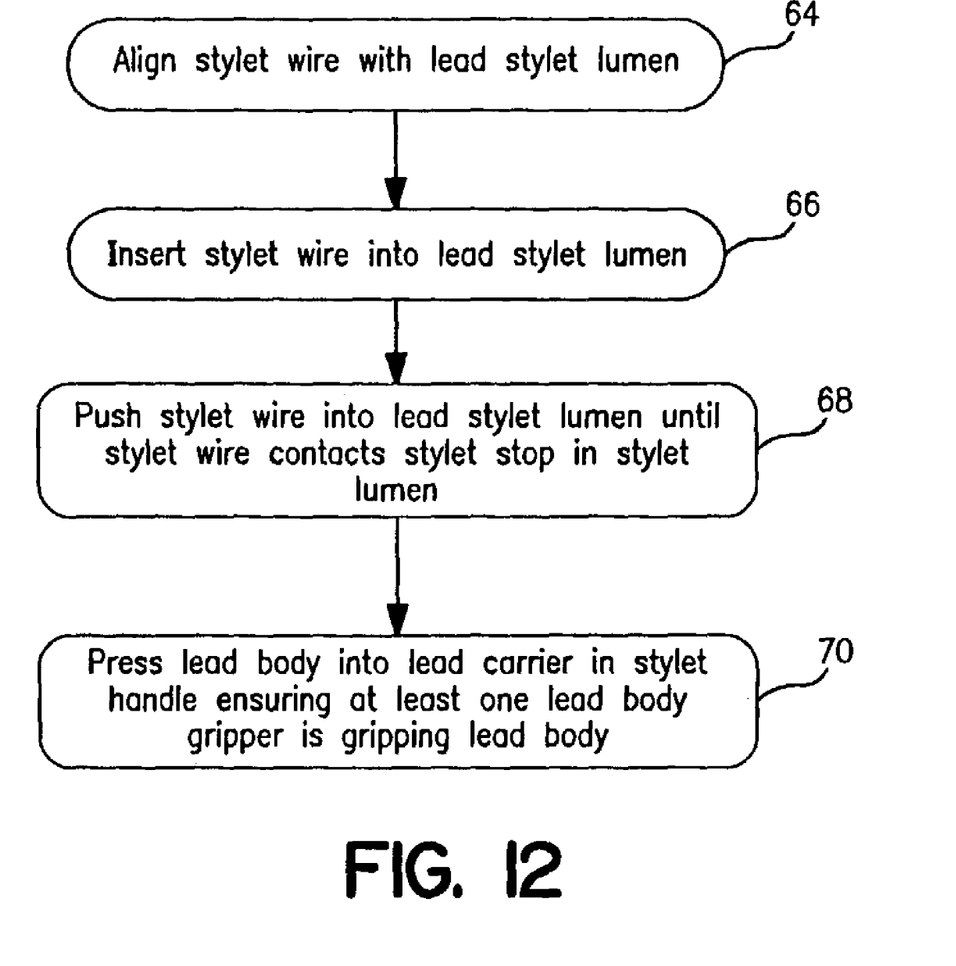

FIG. 12 shows a flowchart of a method for inserting a stylet 50 in a neurological stimulation lead 40. The method begins by aligning 64 a stylet wire 54 with a stylet lumen 48 of a lead body proximal end 45. Once aligned, the stylet wire 54 is inserted 66 into the stylet lumen 48. The stylet wire 54 is pushed 68 through the stylet lumen until the stylet wire 54 contacts a stylet stop 49 in the stylet lumen 48 of a lead body distal end 41. The stylet stop 49 controls where the stylet wire 54 terminates in the stimulation lead 40. With the use of a stylet stop 49 every stimulation lead 40 will have the stylet wire 54 terminate at the same position. This increases the consistency of maneuvering the stimulation lead 40 in the body 28 by a clinician. Once the stylet wire 54 is fully inserted, the lead body 43 is pressed 70 into the lead carrier 56 in the stylet handle 52 by pressing the lead body 43 into the lead carrier 56 using the thumb or forefinger. The lead carrier 56 is designed so a thumb or forefinger has room to push the stimulation lead 40 into the lead carrier 56. By pushing the lead body 43 into the lead carrier 56 the lead body 43 is gripped with at least one gripper 58 in the lead carrier 56. The lead body 43 is typically but not exclusively gripped on the lead body proximal end 45. When the stylet wire 54 is engaged in the stylet handle 52 and the stylet wire 54 contacts the stylet stop 49, at least one gripper 58 in the stylet carrier 56 will grip the stimulation lead 40. The stylet 50 does not have to be custom made in order to fit a specific stimulation lead 40. This provides flexibility for clinicians implanting a neurostimulation system 20. During the implantation procedure many clinicians bend the stylet wire 54 to aid in selectively maneuvering the stimulation lead 40. Once a stylet wire 54 is bent it cannot be easily returned to the original configuration. It is possible to use several stylets 50 during the implantation procedure. The stylet 50 described in this document allows easy replacement of the any stylet 50 with a new stylet 50.

Thus, embodiments of the stimulation lead stylet handle are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable neurological stimulation lead with improved stylet handle, comprising:
   a lead body having a body proximal end, a body distal end, and a stylet lumen;
   at least one conductor contained in the lead extending from the body proximal end to the body distal end, the conductor being electrically insulated;
   at least one electrical connector carried on the body proximal end and electrically connected to the conductor;
   at least one electrode carried on the body distal end and electrically connected to the conductor;
   a stylet wire configured for insertion into the stylet lumen to stiffen the lead body; and
   a stylet handle connected to the stylet wire, wherein the stylet handle defines a lead carrier with a channel-like recess to receive the lead body when the lead body is pushed laterally into the channel-like recess, and includes one or more members that protrude into the channel-like recess to hold the lead body at any selected point along substantially the entire length of the lead body between the body distal end and the body proximal end.

2. The implantable neurological stimulation lead as in claim 1, wherein the selected point is any point along the lead body other than the lead body distal end.

3. The implantable neurological stimulation lead as in claim 1, further comprising a stylet stop in the lead distal end for the stylet wire to contact before the lead body is held in the lead carrier.

4. The implantable neurological stimulation lead as in claim 1, further comprising a stylet release in the stylet handle, the stylet release having an engaged position where the stylet wire is coupled to the stylet handle and a disengaged position where the stylet wire is decoupled from the stylet handle creating a lead opening to permit the stylet handle to be moved toward the lead distal end without being encumbered by the stylet wire.

5. An implantable neurological stimulation lead with improved stylet handle, comprising:
   a lead body having a body proximal end, a body distal end, and a stylet lumen;
   at least one conductor contained in the lead extending from the body proximal end to the body distal end, the conductor being electrically insulated;
   at least one electrical connector carried on the body proximal end and electrically connected to the conductor;
   at least one electrode carried on the body distal end and electrically connected to the conductor;
   a stylet wire configured for insertion into the stylet lumen to stiffen the lead body; and
   stylet handle means for holding the lead body selectively connected to the stylet wire at any selected point along substantially the entire length of the lead body between the body distal end and the body proximal end, wherein the stylet handle means defines a lead carrier with a channel-like recess to receive the lead body when the lead body is pushed laterally into the channel-like recess, and includes one or more members that protrude into the channel-like recess to hold the lead body.

6. A stylet for an implantable neurological stimulation lead, comprising:
   a stylet wire configured for insertion into a stylet lumen to stiffen a lead body; and
   a stylet handle connected to the stylet wire, wherein the stylet handle defines a lead carrier with a channel-like recess to receive the lead body when the lead body is pushed laterally into the channel-like recess, and includes one or more members that protrude into the channel-like recess to hold the lead body at any selected point along substantially the entire length of the lead body between a distal end of the lead body and a proximal end of the lead body.

7. The stylet as in claim 6, wherein the selected point is any point along the lead body other than the lead body proximal end.

8. The stylet as in claim 6, further comprising a stylet release in the stylet handle, the stylet release having an engaged position where the stylet wire is coupled to the stylet handle and a disengaged position where the stylet wire is decoupled from the stylet handle creating a lead opening to permit the stylet handle to be moved toward the lead distal end without being encumbered by the stylet wire.

9. A stylet for an implantable neurological stimulation lead, comprising:
   a stylet wire configured for insertion into a stylet lumen to stiffen a lead body; and
   a means for holding the lead body selectively connected to the stylet wire, the means for holding defining a channel-like recess to receive the lead body when the lead body is pushed laterally into the channel-like recess, and including one or more members that protrude into the channel-like recess to hold the lead body at any selected point along substantially the entire length of the lead body between a distal end of the lead body and a proximal end of the lead body.

10. A method for inserting a stylet in a neurological stimulation lead, comprising:
    aligning a stylet wire with a stylet lumen of a lead body proximal end;
    inserting the stylet wire into the stylet lumen;
    stopping insertion of the stylet wire when the stylet wire contacts a stylet stop in the stylet lumen of a lead body distal end;
    inserting the lead body in a stylet handle lead carrier; and
    holding the lead body at any selected point along substantially the entire length of the lead body between a lead body distal end of and the lead body proximal end within a channel-like recess located in the stylet handle lead carrier when the lead body is pushed laterally into the channel-like recess, while the stylet wire remains in contact with the stylet stop in the stylet lumen in the lead body distal end, wherein the stylet handle lead carrier further includes one or more members that protrude into the channel-like recess to hold the lead body.

11. The method as in claim 10 wherein the lead body is held on the lead body proximal end.

12. A device for implanting a neurostimulation lead, the device comprising:
- a stylet wire for insertion into a stylet lumen in a neurostimulation lead; and
- a stylet handle connected to the stylet wire, the stylet handle having a lead carrier to hold the lead at a selected point along the lead, wherein the lead carrier defines a channel-like recess to receive the lead when the lead is pushed laterally into the channel-like recess, and one or more members that extend into the channel-like recess, and wherein the stylet handle includes a lead opening to accommodate the lead and permit the stylet handle to be moved toward a distal end of the lead.

13. The device of claim 12, wherein the members narrow a width of a portion of the channel.

* * * * *